(12) United States Patent
Mikulowski et al.

(10) Patent No.: US 10,952,714 B1
(45) Date of Patent: Mar. 23, 2021

(54) APPARATUS, METHODS AND SYSTEMS FOR SPINE SURGERY

(71) Applicant: OrtoWay AB, Djursholm (SE)

(72) Inventors: Stan Mikulowski, Djursholm (SE); Staffan Bowald, Fjardhundra (SE)

(73) Assignee: OrtoWay AB, Djursholm (SE)

( * ) Notice: Subject to any disclaimer, the term of this patent is extended or adjusted under 35 U.S.C. 154(b) by 128 days.

(21) Appl. No.: 16/036,916

(22) Filed: Jul. 16, 2018

Related U.S. Application Data

(60) Provisional application No. 62/532,562, filed on Jul. 14, 2017.

(51) Int. Cl.
| | |
|---|---|
| *A61B 17/02* | (2006.01) |
| *A61F 2/46* | (2006.01) |
| *A61B 17/86* | (2006.01) |
| *A61F 2/44* | (2006.01) |
| *A61B 17/70* | (2006.01) |

(52) U.S. Cl.
CPC ............ *A61B 17/025* (2013.01); *A61B 17/86* (2013.01); *A61F 2/441* (2013.01); *A61F 2/4611* (2013.01); *A61B 17/70* (2013.01); *A61B 2017/0256* (2013.01); *A61F 2002/4622* (2013.01)

(58) Field of Classification Search
CPC .................. A61B 17/02; A61B 17/025; A61B 2017/0256; A61B 2017/0262; A61B 17/86; A61F 2/441; A61F 2002/4611
See application file for complete search history.

(56) References Cited

U.S. PATENT DOCUMENTS

| | | |
|---|---|---|
| 2,371,519 A | 3/1945 | Haynes |
| 4,386,603 A | 6/1983 | Mayfield |
| 4,611,580 A | 9/1986 | Wu |
| 4,658,809 A | 4/1987 | Ulrich et al. |
| 4,733,657 A | 3/1988 | Kluger |
| 4,854,304 A | 8/1989 | Zielke |
| 4,944,743 A | 7/1990 | Gotzen et al. |

(Continued)

FOREIGN PATENT DOCUMENTS

| | | |
|---|---|---|
| EP | 0978258 A1 | 2/2000 |
| WO | WO 1990/002527 A1 | 3/1990 |
| WO | WO 2006/130085 A1 | 12/2006 |

OTHER PUBLICATIONS

International Search Report for International Application No. PCT/SE2009/000275, dated Sep. 11, 2009, 6 pages.

(Continued)

*Primary Examiner* — Eric S Gibson
(74) *Attorney, Agent, or Firm* — Cooley LLP

(57) ABSTRACT

Embodiments of a corpectomy method, comprising the steps of: providing a distractor unit comprising at least a first hydraulic cylinder configured to removably receive a piston of a predetermined length during a surgical procedure; providing the piston; providing a plurality of bone screws; affixing a first bone screw of the plurality of bone screws to a first vertebrae of a spine and a second bone screw of the plurality of bone screws to a second vertebrae of the spine; mounting the distractor unit onto the first bone screw and the second bone screw; and extending the hydraulic piston of the distractor unit to cause the first vertebrae and the second vertebrae to move away from each other are disclosed.

20 Claims, 18 Drawing Sheets

(56) References Cited

U.S. PATENT DOCUMENTS

| | | | |
|---|---|---|---|
| 5,219,349 A | 6/1993 | Krag et al. | |
| 5,304,179 A | 4/1994 | Wagner | |
| 5,431,658 A | 7/1995 | Moskovch | |
| 6,139,493 A * | 10/2000 | Koros | A61B 17/0206 600/213 |
| 6,565,568 B1 | 5/2003 | Rogozinski | |
| 7,387,635 B2 | 6/2008 | Keller | |
| 8,764,800 B2 | 7/2014 | Johansson et al. | |
| 9,049,989 B2 * | 6/2015 | Crenshaw | A61B 17/0218 |
| 9,615,938 B2 * | 4/2017 | Frey | A61F 2/4455 |
| 10,159,475 B2 * | 12/2018 | Frey | A61B 17/56 |
| 10,368,854 B2 * | 8/2019 | Pell | A61B 17/0206 |
| 2003/0055427 A1 | 3/2003 | Graf | |
| 2003/0181800 A1 * | 9/2003 | Bonutti | A61B 90/39 600/407 |
| 2003/0236472 A1 * | 12/2003 | Van Hoeck | A61B 17/0206 600/587 |
| 2004/0002758 A1 | 1/2004 | Landry et al. | |
| 2004/0059271 A1 | 3/2004 | Berry | |
| 2004/0148028 A1 | 7/2004 | Ferree et al. | |
| 2004/0220567 A1 | 11/2004 | Eisermann et al. | |
| 2004/0220582 A1 | 11/2004 | Keller | |
| 2004/0225295 A1 | 11/2004 | Zubok et al. | |
| 2005/0159651 A1 | 7/2005 | Raymond et al. | |
| 2005/0177156 A1 | 8/2005 | Timm et al. | |
| 2005/0203532 A1 | 9/2005 | Ferguson et al. | |
| 2005/0245928 A1 | 11/2005 | Colleran et al. | |
| 2008/0077155 A1 | 3/2008 | Diederich et al. | |
| 2008/0172062 A1 | 7/2008 | Donahue et al. | |
| 2009/0259107 A1 * | 10/2009 | Crenshaw | A61B 7/00 600/202 |
| 2012/0130180 A1 * | 5/2012 | Pell | A61B 17/025 600/206 |
| 2012/0136355 A1 | 5/2012 | Wolfson | |
| 2012/0184958 A1 | 7/2012 | Knuchel et al. | |
| 2014/0257313 A1 * | 9/2014 | Frey | A61B 2/4601 606/90 |
| 2016/0007983 A1 * | 1/2016 | Frey | A61B 17/8009 623/17.16 |
| 2016/0213500 A1 * | 7/2016 | Beger | A61B 17/025 |
| 2017/0209287 A1 * | 7/2017 | Frey | A61F 2/4455 |
| 2020/0093614 A1 * | 3/2020 | Arramon | A61F 2/4657 |
| 2020/0113713 A1 * | 4/2020 | LaMarca | A61F 2/30749 |

OTHER PUBLICATIONS

Written Opinion of the International Searching Authority for International Application No. PCT/SE2009/000275, dated Sep. 11, 2009, 7 pages.

International Preliminary Report on Patentability for International Application No. PCT/SE2009/000275, dated Aug. 11, 2010, 9 pages.

Extended European Search Report for European Application No. 09755134.5, dated Apr. 25, 2013, 6 pages.

Medtronic, "Cornerstone—SR Cervical Carbon Cage System", Announcement Medtronic., Jan. 1, 1998, pp. 1-11, XP007916830.

* cited by examiner

Awl for marking the position of the bones screws.

Bone screws, 4 pcs, with protective

*Bone screwdriver to fasten the bone screws,*

*Offset screwdriver for perpendicular fixation of the Distractor against the bone screw,*

*Lock screwdriver for vertical fixation of the Distractor against the bone screw,*

Spacer unit for adjusting the distance between the bone screws.

Positioning screwdriver for replacing the push rod (L).

APPARATUS, METHODS AND SYSTEMS FOR SPINE SURGERY

CROSS REFERENCE TO RELATED APPLICATIONS

This application claims priority to and the benefit of U.S. Provisional Patent Application No. 62/532,562, filed Jul. 14, 2017, entitled "Methods and Systems for Anterior Surgery", which is incorporated by reference herein in its entirety.

FIELD OF THE DISCLOSURE

Embodiments of the current disclosure are directed toward an apparatus, methods and systems for spine surgery, and more particularly, an apparatus, methods and systems for separating vertebra during anterior and lateral surgeries.

BACKGROUND

Surgical operations have been increasingly employed to deal with complications that arise from disc degenerations in patients. For example, fusion operations can be performed to treat such complications, resulting in an ossified connection of vertebrae. Alternatively, or in addition to fusion, disc implants can be used to replace the degenerated disc. In contrast to fusion, this approach has the advantage of preserving the movability of the vertebra adjacent to the defective disc.

SUMMARY OF SOME OF THE EMBODIMENTS

Some embodiments of the current disclosure disclose a corpectomy method, comprising the steps of: providing a distractor unit comprising at least a first hydraulic cylinder configured to removably receive a piston of a predetermined length during a surgical procedure; providing the piston; providing a plurality of bone screws; affixing a first bone screw of the plurality of bone screws to a first vertebrae of a spine and a second bone screw of the plurality of bone screws to a second vertebrae of the spine; mounting the distractor unit onto the first bone screw and the second bone screw; and extending the hydraulic piston of the distractor unit to cause the first vertebrae and the second vertebrae to move away from each other.

Some embodiments of the current disclosure disclose a vertebral separation method comprising the steps of: notching at least one pair of vertebrae to mark at least two pairs of positions for inserting bone screws at a lateral distance apart from a center of an anterior spinal column; inserting the bone screws into the at least one pair of vertebrae at the notched positions, the insertion configured at an angle relative to a longitudinal axis of the spinal column so as to avoid penetrating a spinal canal, and such that the bone screws enter, but not go through, opposite cortical bone tissue; mounting a suitably sized spacer ring to each of the bone screws; attaching a distractor unit to each pair of the bone screws in a substantially vertical position at a desired angle relative to an anterior side of the spinal column; locking each distractor unit at the desired angle against each pair of the bone screws; and separating the at least one pair of vertebrae by extending a hydraulic piston within the distractor unit such that the bone screws are moved away from each other.

Such embodiments may include one and/or another (and also, a plurality of) of the following features, structures, functionalities, steps, and/or clarifications, yielding yet still other embodiments of the present disclosure:

providing a retractor, coupling the retractor to the distractor unit, and expanding the retractor to isolate the spine from at least some surrounding tissues;

where such a retractor can include a frame configured to exert force on the retractor to cause its expansion;

where such a retractor comprises a material that is at least translucent to X-rays;

a spanner handle configured for controlling a pressure in the hydraulic cylinder;

a pressure gauge configured for monitoring the pressure in the hydraulic cylinder;

where the first vertebrae of the spine and the second vertebrae of the spine are neighboring vertebra;

where at least one vertebrae exists between the first vertebrae of the spine and the second vertebrae of the spine;

where the length of the hydraulic piston ranges from about 70 mm to about 110 mm;

where the hydraulic piston is replaceable; and removing at least a part of a vertebral body located between the first vertebrae and the second vertebrae.

Some embodiments of the current disclosure disclose a distractor system including a mostly non-disposable surgical system with some disposable components, configured to at least one of separate, hold apart, and reposition vertebrae during surgery. The distractor system provides a fine control of separation distance between vertebra, facilitating enhanced positioning of, for example, a prosthesis. In some embodiments, the distractor system includes a distractor unit, a hydraulic tube unit, a spanner handle, retractors and frame, measurement gauge, a plurality of hooks, a plurality of bone screws and additional tools such as screw drivers and the like.

Such embodiments may include one and/or another (and also, a plurality of) of the following features, structures, functionalities, steps, and/or clarifications, yielding yet still other embodiments of the present disclosure:

where the distractor unit includes a handle configured to effect pressure control on the hydraulic piston and movement thereof;

where pressure is increased alternately between the distractor units located on opposite sides, and the lateral distance, apart from the center of an anterior spinal column;

where pressure is monitored via a pressure gauge included with one and/or another distractor unit;

positioning one or more retractors to tissue, wherein the retractors are configured to separate soft tissue;

where the retractors are placed in designated openings/holes in each distractor unit;

positioning a frame between the retractors, wherein the frame is configured to improve accessibility to the spine; and performing a procedure selected from the group consisting of: corpectomy, insertion of disc prostheses, insertion of an anterior lumbar interbody fusion (ALIF) cage, and tumor removal; and adjusting a gap between the vertebrae by moving the hydraulic pistons.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1A:
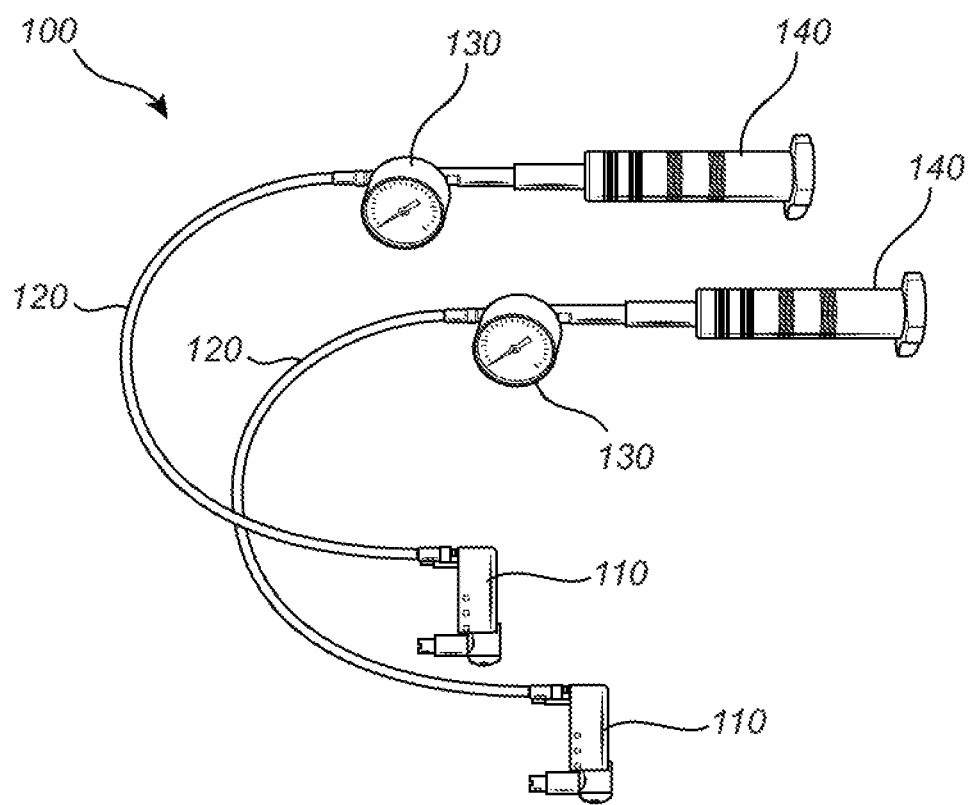
FIGS. 1A-B show an example hydraulic spinal distractor configured to provide control over distances between adjacent or nearby vertebra during spine surgery, according to some embodiments.
Figure 1B:
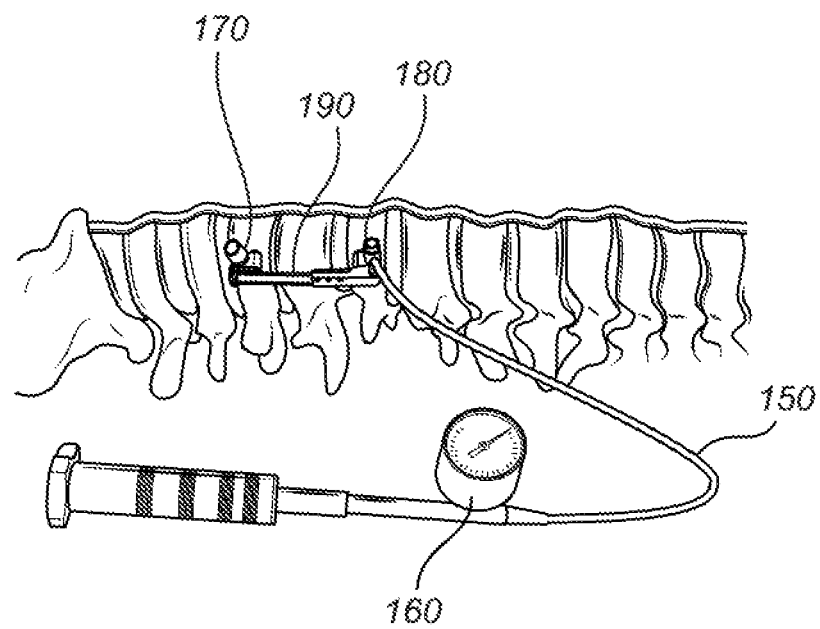

FIGS. 1A-B show an example hydraulic spinal distractor configured to provide control over distances between adjacent or nearby vertebra during spine surgery, according to some embodiments. In some embodiments, with reference to FIG. 1A, the distractor apparatus 100 comprises a distractor unit 110, a hydraulic tube unit 120, a measurement gauge 130 and a spanner handle 140 for controlling the pressure in the measurement gauge 130. In some embodiments, one or more of the distractor unit 110 and the spanner handle 140 may be configured to be non-disposable while one or more of the hydraulic tube unit 120 and the measurement gauge 130 may be configured to be disposable. In some embodiments, the distractor unit 110 may be attached to adjacent vertebrae or vertebrae that are near to each other (i.e., non-neighboring but close vertebra). For example, as discussed below, the distractor unit 110 may be attached to a vertebrae via a bone screw secured to a part of the vertebrae. Using the spanner handle 140, in some embodiments, the pressure in the hydraulic tube unit 120 may be changed, varying the length of the distractor unit 110 and consequently the separation distance between vertebrae attached to the distractor unit 110. For example, with reference to FIG. 1B, by increasing or decreasing the pressure in the hydraulic tube unit 150, as measured by the measurement gauge 160, in some embodiments, the separation distance between the vertebrae 170, 180 that are attached to the distractor unit 190 may be controlled (e.g., increased or decreased), facilitating access to discs (and/or vertebrae) located therebetween. In some embodiments, the changes in the pressure may be restricted within a predefined range to avoid over-separation of vertebrae and possible damages to surrounding tissues. In some embodiments, the discs may be damaged, and the distractor 100 may ease access to the discs to facilitate their removal and/or implantation of disc or spinal cage prostheses. As an example, the distractor 100 may be used during corpectomy (which may include lateral corpectomy in some embodiments) where part or all of a vertebral body is removed. Further, by separating and holding apart vertebrae 170, 180, in some embodiments, the distractor 100 facilitates the repositioning of vertebral bodies therebetween or in the vicinity following implantation of the disc or cage prostheses. In general, the detractor 100 can be used for anterior and/or lateral surgical procedures that include steps for controlling the separation, positioning and/or stability of vertebra. For example, the detractor can be used to access damaged discs or vertebra in procedures to treat scoliosis/spinal deformities. Additional examples include the detractor 100 being used during discectomy including multi-level discectomy, during procedures to insert disc prosthesis and/or anterior lumbar interbody fusion (ALIF) cages, and during tumor surgeries. In addition, the detractor 100 can also be used to control the positioning of iliac arteries and veins during surgeries (e.g., during surgeries in the region inferior to the aortic bifurcation).

In some embodiments, the disposable components of the vertebral separation system disclosed herein such as but not limited to the tube unit, the measurement gauge, hooks for attaching the retractor to the distractor unit, the bone screws, etc., may be packaged separately from the non-disposable components such as but not limited to the distractor unit, the spanner handle, the retractors, the frame, and the various tools (e.g., bone screw drivers, etc.). Some embodiments of the current disclosure are directed to a kit comprising the disposable components and the non-disposable components.

With reference to FIGS. 2A-F, in some embodiments, various rotational ranges of the distractor unit of a hydraulic spinal distractor system facilitating a fine-tuned control of the separation between adjacent or nearby vertebrae are shown. In some embodiments, the distractor unit 200 comprises a first jointed part 210 and a second jointed part 240, each jointed part including a pair of arms that are connected via a joint, e.g., FIG. 2A. The first arm of one of the first jointed part 210 and the second jointed part 240 may include a fully or partially hollow interior configured for receiving a second arm of the other of the first jointed part 210 and the second jointed part 240. For example, the first jointed part 210 may include a first arm 230 that has a hollow interior configured for receiving the second arm 260 of the second jointed part 240, the second arm 260 being complementary with the first arm 230 and having the size and shape configured for mating with the hollow interior of the first arm 230, e.g., FIG. 2B (or vice versa). For example, the first arm 230 and the second arm 260 may make up a hydraulic piston system. In particular, the first arm 230 may be a hydraulic cylinder and the second arm 260 may be a piston.

In some embodiments, the second arm of one of the first jointed part 210 and the second jointed part 240 may include a hollow interior configured for receiving a bone screw for attachment with a vertebrae. For example, the first jointed part 210 and/or the second jointed part 240 may respectively include a second arm 220 and/or 250 that are configured to allow a bone screw to pass through their interiors for attachment with vertebra, thereby allowing the distractor unit 200 (which includes the first jointed part 210 and the second jointed part 240) to be coupled to the vertebrae.

In some embodiments, with the second arms 220 and 250 coupled to the bone screws affixed to vertebra, the distance between the vertebra may correspond at least substantially with the distance between the second arms 220 and 250 (as measured from the joints 270 and 280, for example). In such embodiments, the distance between the vertebra may be varied (for example, to access a damaged disc between the vertebra) by varying the distance between the second arms 220 and 250. In some embodiments, the distance between the second arms 220 and 250 may be varied based on the extent of the second arm 260's penetration into the hollow interior of the first arm 230. For example, the mating between the second arm 260 and the first arm 230 may be configured such that the distance the second arm 260 traverses within the hollow interior of the first arm 230 before being secured to the first arm 230 (and its motion within the first arm 230 ceased) may be variable, either continuously or step-wise. That is, the hydraulic piston system comprising the first arm 230 and the second arm 260 may change its length continuously or in a step-wise fashion based on the distance the first arm 230 traverses as it enters the second arm 260.

For example, as discussed above, in some embodiments, the first arm 230 and the second arm 260 may make up a hydraulic piston system, and the separation distance between the second arms 220 and 250 may correspond at least substantially to the length of the hydraulic piston system. In such embodiments, the separation distance can be controlled by selecting an appropriately sized piston and/or by controlling the extension of the piston (for example, by varying the pressure within the hydraulic tube units that deliver/withdraw pressure to the piston and cause/reduce its extension). In some embodiments, the second arm 260 (e.g., the piston) may be replaceable and the separation distance between the vertebra may be varied by using different length second arm 260 or pistons. For example, in some embodiments, the second arm 260 or the pistons may have a length ranging from about 30 mm to about 120 mm, from about 40 mm to about 100 mm, from about 50 mm to about 90 mm, from about 60 mm to about 80 mm, about 37 mm, about 47 mm, about 57 mm, about 77 mm, about 87 mm, about 100 mm, including values and subranges therebetween. By selecting a piston with desired length, in some embodiments, the length of the hydraulic piston system may be varied, facilitating the control of the vertebra separation distance. In some embodiments, the hydraulic piston system may be extended by increasing the pressure in the hydraulic tube of the distractor with the use of the spanner handle.

As an example illustration of the above embodiments, the second arms 220 and 250 may be coupled to adjacent vertebrae via bone screws, the adjacent vertebrae sandwiching a damaged disk. To access the damaged disc with ease, the distance between the second arms 220 and 250 may be increased by using a longer piston and/or extending the hydraulic piston system as discussed above, for example, thereby increasing the distance between the neighboring vertebrae and providing access to the damaged disc.

Figure 2A:
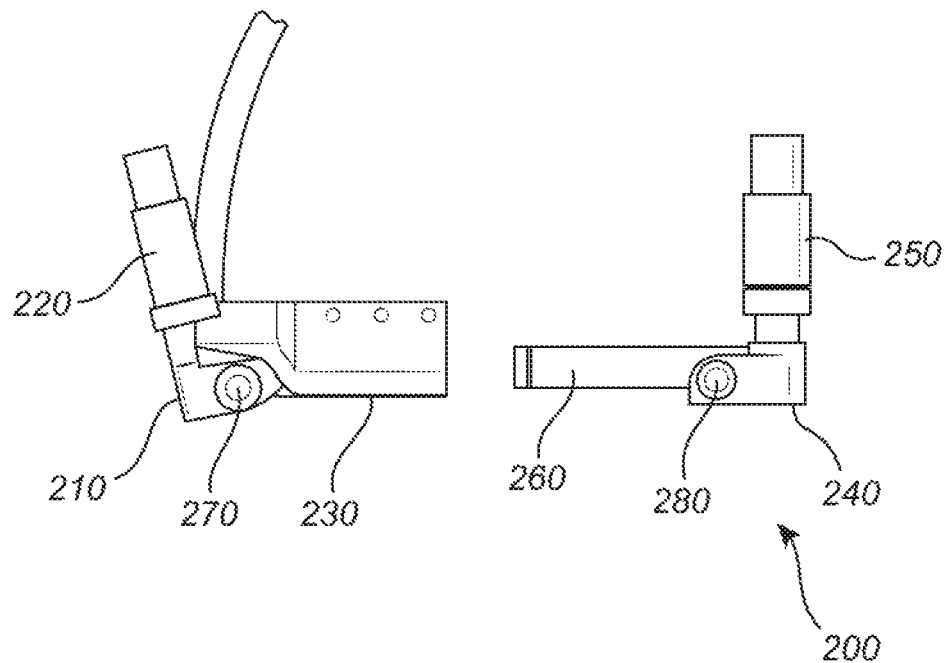
FIGS. 2A-F show the various rotational ranges of the spanner unit of a hydraulic spinal distractor system facilitating a fine-tuned control of the separation between adjacent or nearby vertebrae, according to some embodiments.
Figure 2B:
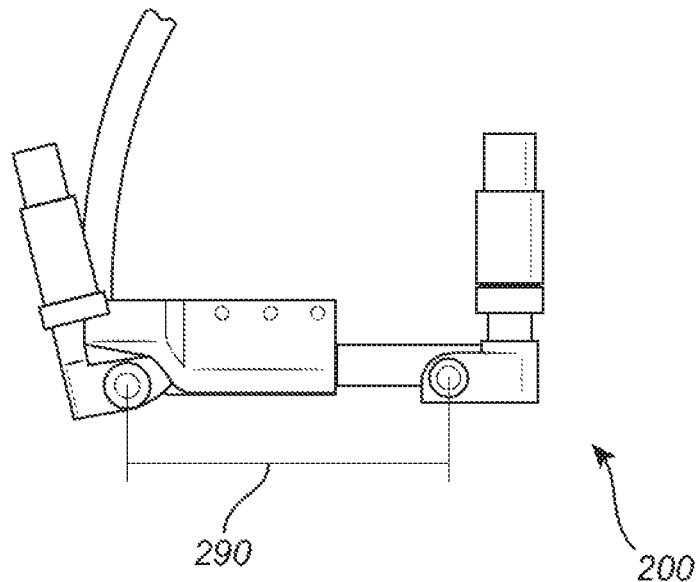
Figure 2C:
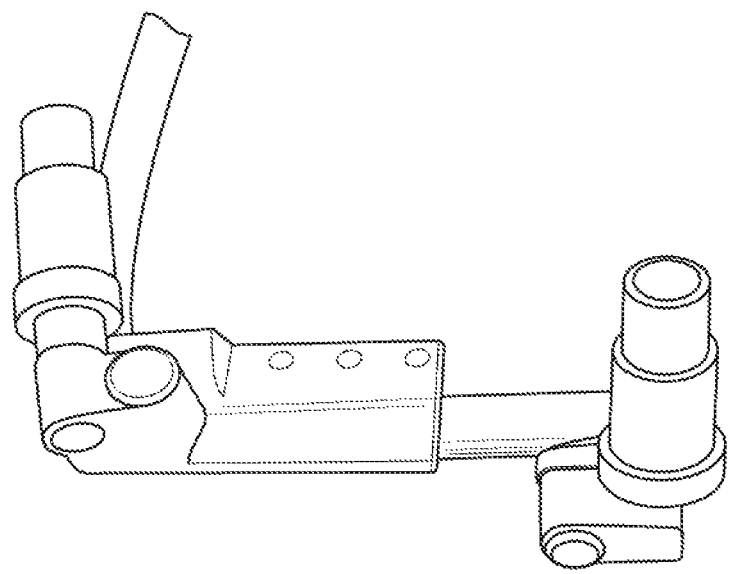
Figure 2D:
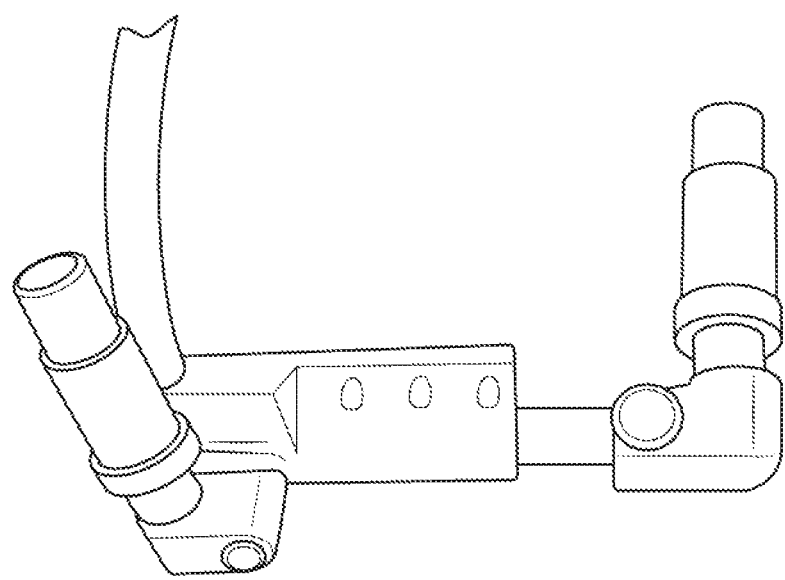
Figure 2E:
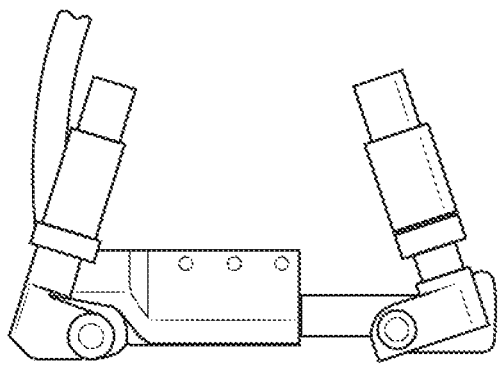
Figure 2F:
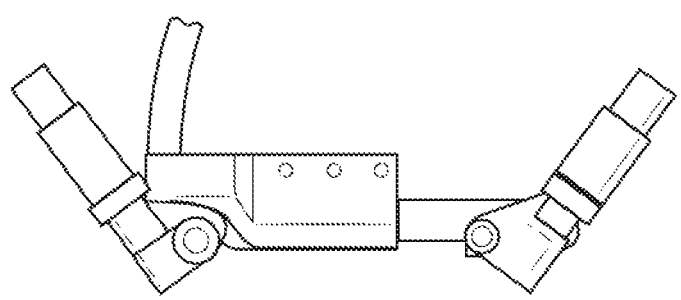

In some embodiments, FIGS. 2C-F illustrate the rotational ranges of the spanner 200 that are allowed by the pivot joints 270 and 280 as well as the longitudinal axis 290 running along between the said pivot joints. For example, FIGS. 2C-D show example twisting rotations where the second arms 220 and 250 rotate in opposite directions with each other. For example, in some embodiments, one of the second arms 220 and 250 may rotate in a clockwise or anticlockwise direction as the other second arm rotates in anticlockwise or clockwise direction, respectively. Such twisting rotations are example embodiments of rotations where either second arm 220, 250 rotates about the longitudinal axis 290. In some embodiments, the second arms 220 and 250 may be configured to rotate, about the longitudinal axis 290. As another example, FIGS. 2E-F show the rotation of the second arms 220, 250 about the joints 270, 280, respectively. In some embodiments, the second arms 220 and 250 may rotate towards each other (FIG. 2E), away from each other (FIG. 2F), or in the same direction (not shown), in the same plane, i.e., in the plane defined by the longitudinal axis 290 and any of the second arms 270, 280. In some embodiments, the second arms 220 and 250 may be configured to rotate, about the respective joints 270 and 280, the angles measured from the longitudinal axis 290 to the second arms 220 and 250, respectively.

Figure 3A:
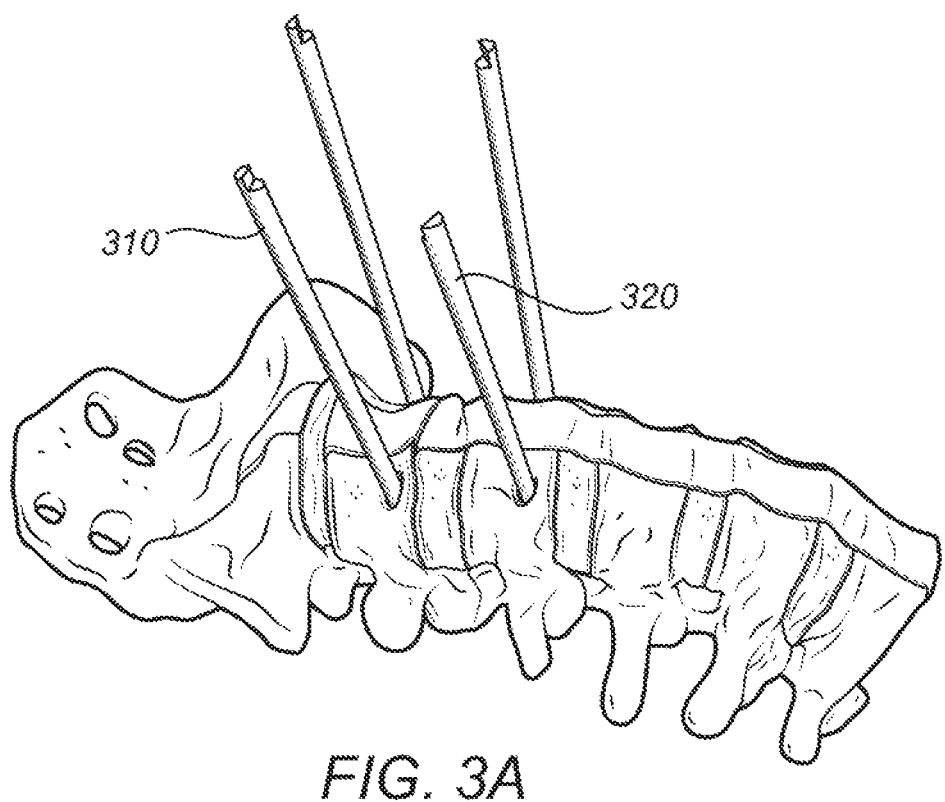
FIGS. 3A-C show the use of screws for attaching the hydraulic spinal distractor of FIGS. 1A-B to vertebrae adjacent or near a defective disc for controlling the distance between the vertebrae, according to some embodiments.
Figure 3B:
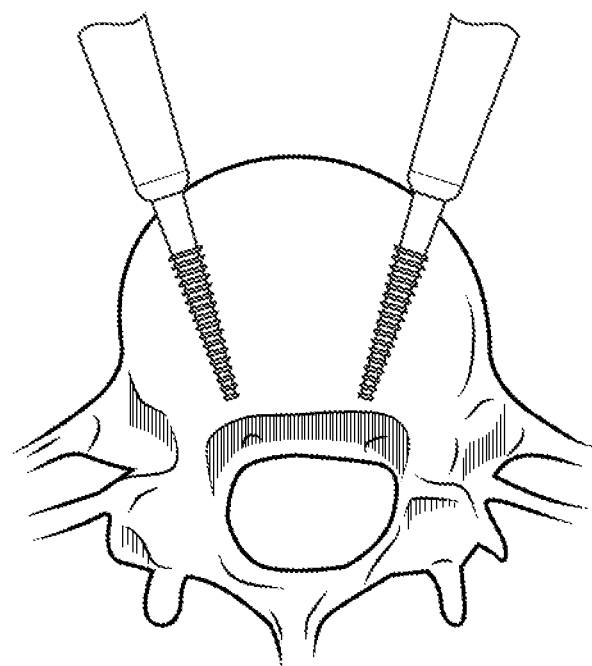
Figure 3C:
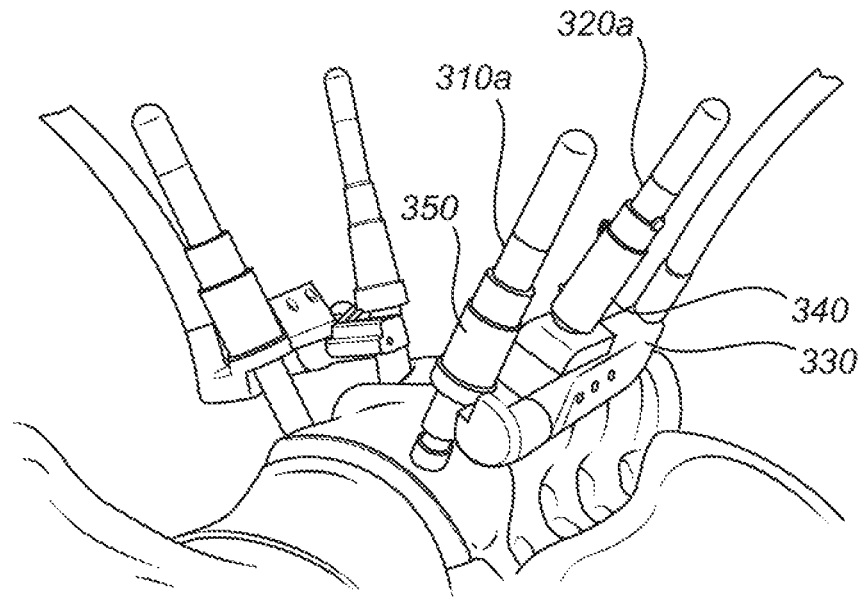

FIGS. 3A-C show the use of screws for attaching the hydraulic spinal distractor of FIGS. 1A-B to vertebrae adjacent or near a defective disc for controlling the separation between the vertebrae, according to some embodiments. As discussed above with reference to FIGS. 2A-F, in some embodiments, the second arms 220 and 250 (which may be hollow hydraulic cylinders) are coupled to vertebra via screws affixed to the vertebra. For example, bone screws 310a, 320a may be affixed to neighboring vertebra or vertebra in proximity to each other where in the former case (e.g., FIG. 3A) the disc in between may be damaged and in the latter case discs and/or vertebra in between may be damaged. In some embodiments, the bone screws may be attached to the ends of vertebrae to increase the strength of attachment between the screws and the vertebrae. For examples, the bone screws may be attached to the vertebrae about 3 mm, about 2.5 mm, about 2 mm, about 1.5 mm, about 1 mm, including values and subranges therebetween, from the ends of the vertebrae. FIG. 3B shows a close-up view of the bone screws embedded within a vertebrae.

Upon securing the bone screws 310 and 320 to different vertebrae, in some embodiments, a hydraulic distractor unit 330 including a first hollow arm 340 and a second hollow arm 350 may be coupled to the bone screws 310 and 320 for controlling the separation distance between the vertebrae as well as positioning and stability of the vertebral body in general, which may lead to increased access to the discs and/or vertebrae therebetween. For example, the first hollow arm 340 and the second hollow arm 350 may be coupled to the bone screws 310 and 320 by allowing the bone screws 310 and 320 to pass through the hollow interiors of the first hollow arm 340 and the second hollow arm 350. In some embodiments, a plurality of pairs of bone screws and distractors may be used for additional control over separation distances and positioning of vertebra. As an example, FIG. 3C shows two pairs of bone screws affixed to vertebra, with a pair on the same side of the vertebrae being coupled to the same distractor unit.

An example application of the apparatus, methods and systems disclosed herein is for discectomy, where a damaged or abnormal disc is surgically removed. In such embodiments, the bone screws and the distractor disclosed herein can be used to control the separation, positioning and stability of vertebra. For example, the bone screws and the distractor may be mounted into the vertebra to separate the vertebra to facilitate the removal of the damaged disc.

Figure 3D:
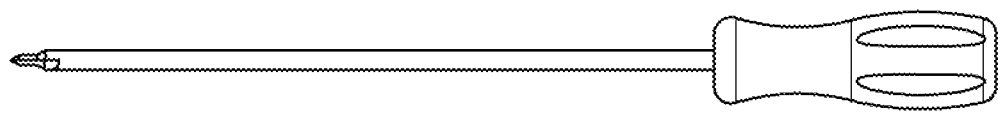
FIGS. 3D-K show example images/schematic of tools used for treating various spinal deformities or damages, including corpectomy, discectomy, surgical procedures for treating scoliosis, etc., according to some embodiments.
Figure 3E:
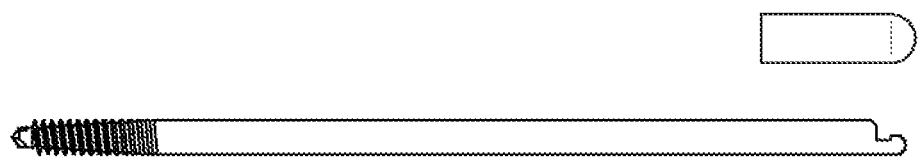
Figure 3F:
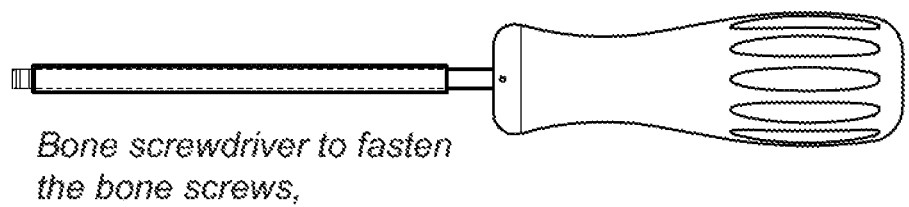
Figure 3G:
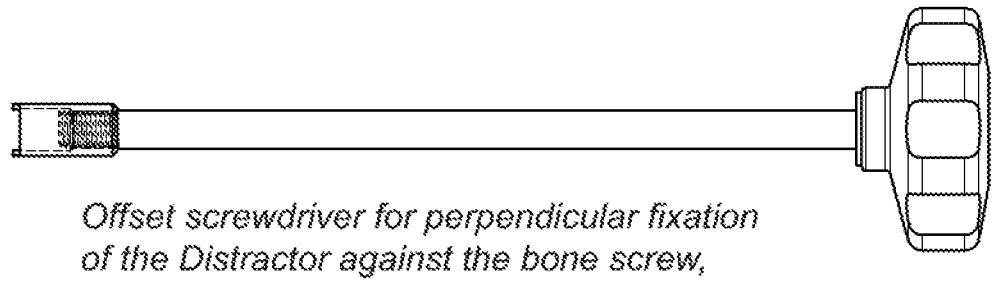
Figure 3H:
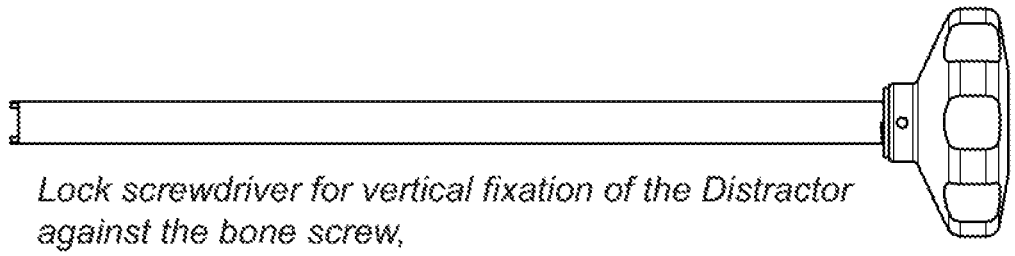
Figure 3I:
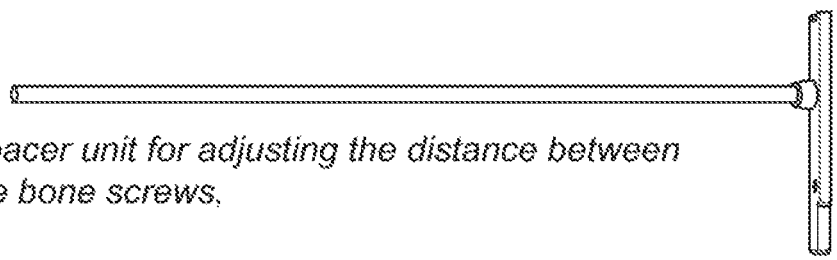
Figure 3J:
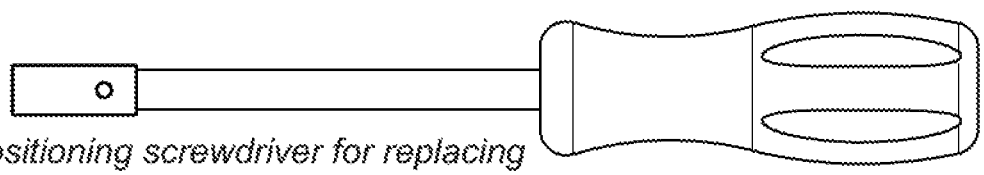
Figure 3K:
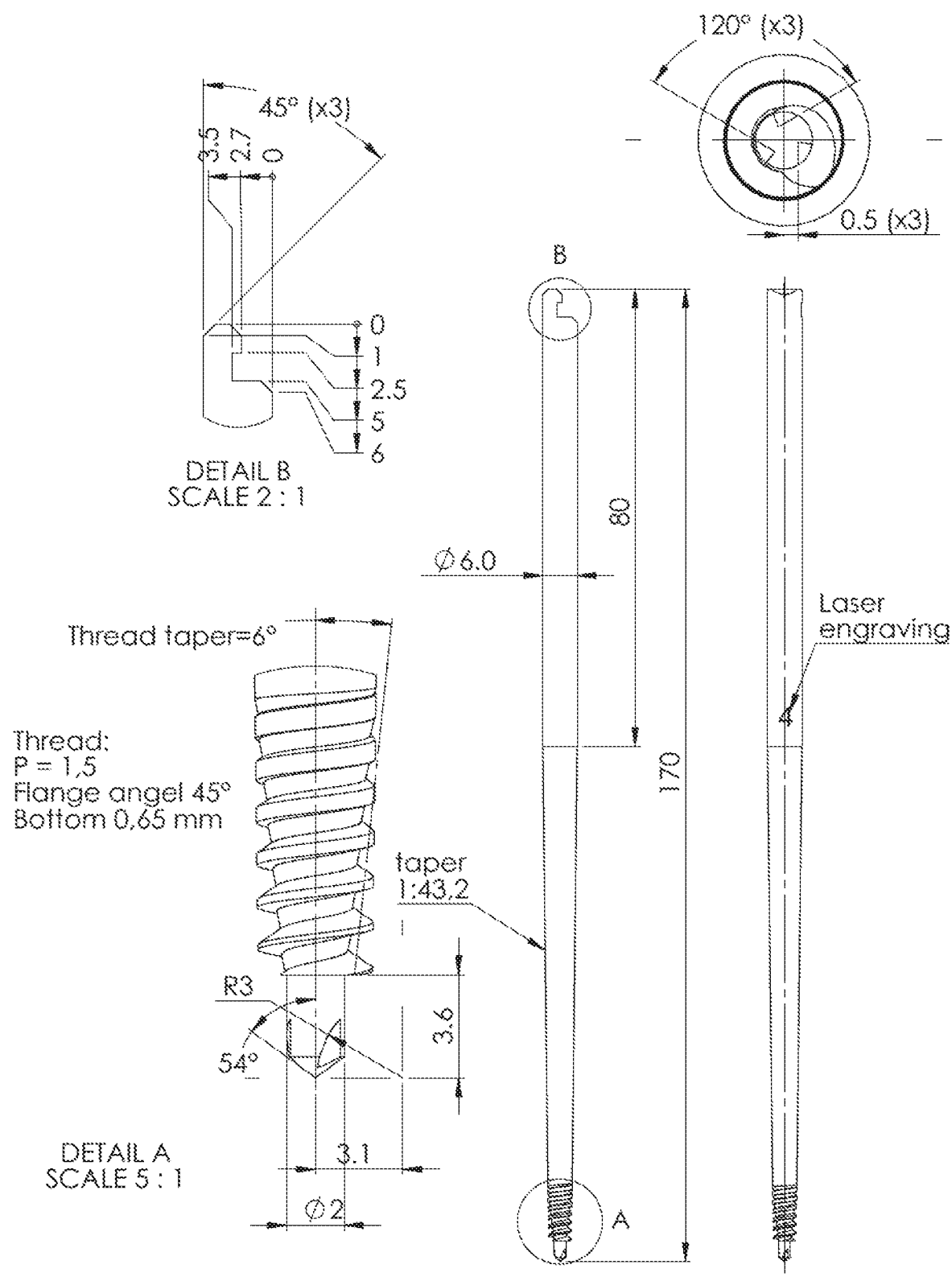

Positioning and Mounting Bone Screws. For ventral surgery, a plurality of screws (e.g., four) and two distractor units can be used (e.g., as shown in FIG. 3C). First, notches can be made in the vertebrae with an awl, for example, to mark the positions of the screws. In some embodiments, the screws can be secured near end plates of the vertebrae, with cages being used, if desired, to protect the surrounding tissues when mounting the screws. In such embodiments, the screws may be angled to avoid penetrating the spinal canal. Further, the bone screws may be affixed to the vertebra without passing through the vertebra (e.g., the position and depth of the screws may be monitored with an X-ray equipment). At least sufficient lateral screw distance may be used to allow the implant to be inserted between hydraulic cylinders (i.e., hollow arms) of the distractor unit. In some embodiments, bone screws of a certain size and/or thread-pitch may be selected based on the particular surgical procedure. For example, in the case of surgery for implanting a rod-system to treat scoliosis, 4.5 cm threaded bone screws may be used. In some embodiments, the size of the threaded bone screw may be about 4 cm, about 4.25 cm, about 4.75 cm, about 5 cm, including values and subranges therebetween. FIGS. 3D-J show example images/schematic of tools, such as but not limited to, bone screws, screw drivers, etc., used for treating various spinal deformities or damages, said treatments including corpectomy, discectomy, surgical procedures for treating scoliosis, etc. For example, FIG. 3D shows an example awl for marking on vertebra positions for attaching or affixing bone screws; FIG. 3E shows example bone screws with protective caps; FIG. 3F shows example bone screw driver configured for fastening the bone screws onto vertebra;

FIG. 3G shows an example offset screw driver configured for perpendicular fixation of distractor units against bone screws; FIG. 3H shows an example lock screw driver configured for vertical fixation of distractor units against bone screws; FIG. 3I shows an example spacer unit configured for adjusting the separation distance between bone screws; and FIG. 3J shows an example positioning screw driver configured for replacing pistons (e.g., when using a longer distractor during corpectomy compared to at least some other procedures). FIG. 3K shows example schematics of such threaded bone screw configured for use in surgical procedures to treat scoliosis, according to some embodiments. In this particular embodiment, the screw may be tapered and the tip may be angled (and tapered as well) to facilitate insertion into vertebra. The dimensions listed in any of the figures including FIG. 3K are intended for illustration purposes and are not limiting in any way.

Figure 4A:
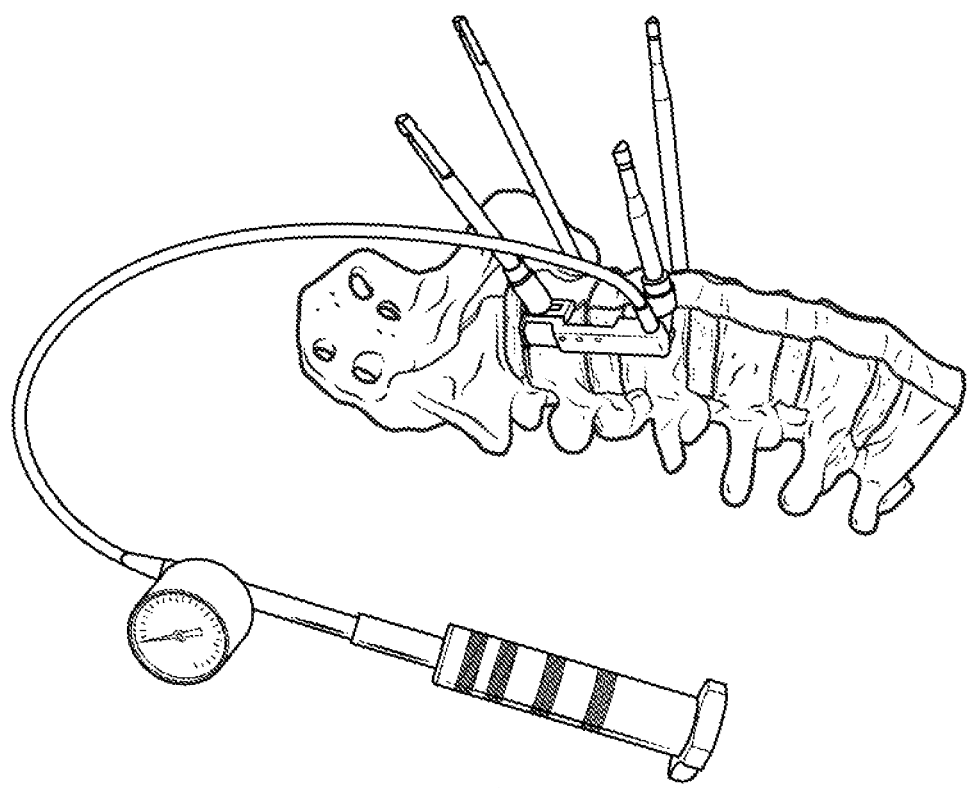
FIG. 4A-D show illustrate example steps for mounting the distractor disclosed herein onto vertebrae, according to some embodiments.
Figure 4B:
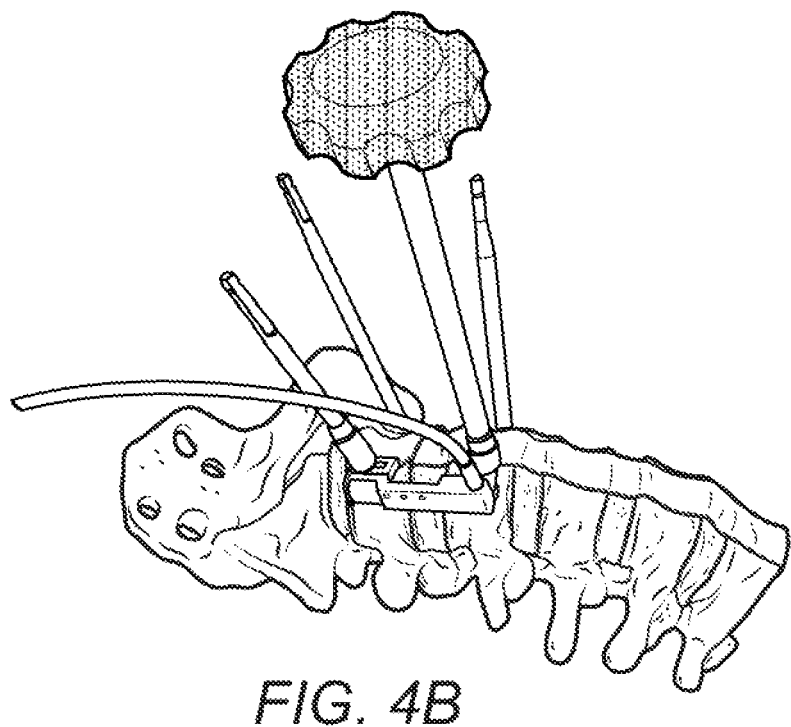
Figure 4C:
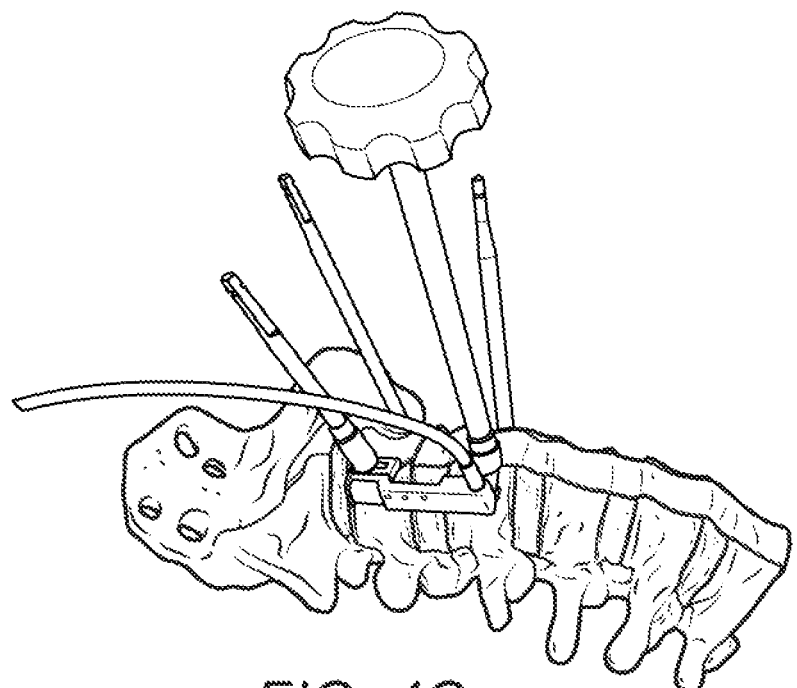

Mounting of Distractor Units. In some embodiments, prior to mounting a distractor unit, any protective cages may be removed from the screws and spacer rings of suitable length may be mounted. Then, distractor units may be attached on bone screws, paired in the longitudinal direction of the vertebral column, as shown in FIG. 4A, for example. In some embodiments, the distractor units may be positioned laterally, away from the middle of the spine, and at least substantially vertical. Using a lock screwdriver, such as the one depicted in FIG. 3H, for example, the distractor units may be locked with the plurality of bone screws, as shown in the example embodiment of FIG. 4B. Further, with the use of an offset screwdriver, such as the one depicted in FIG. 3G, in some embodiments, the distractor units can be locked at desired angles against the bone screws (e.g., FIG. 4C). In some embodiments, the angles may be altered during the surgical procedure.

Figure 4D:
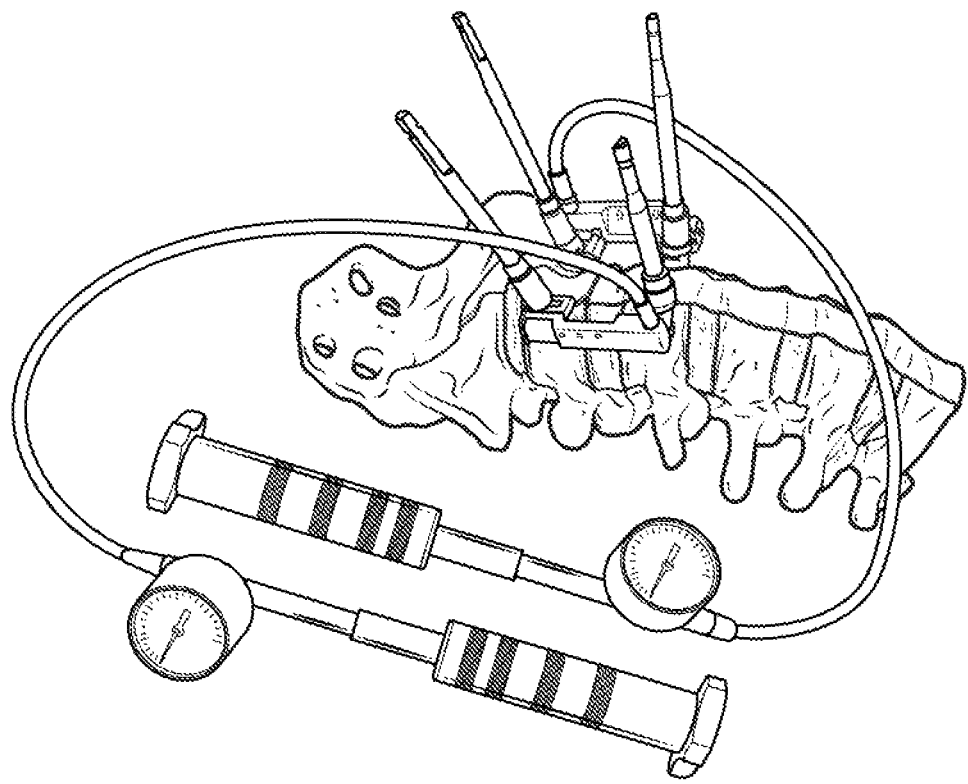

Separating Vertebrae. To separate vertebrae coupled to distractor units, in some embodiments, the handles of the distractor (such as handle 140 in FIG. 1A) may be used to control pressure within the hydraulic tube of the distractor (e.g., hydraulic tube unit 120 in FIG. 1A). For example, the handle may be used to extend pistons of the distractor units so as to increase pressure incrementally to separate the vertebrae. In some embodiments, pressure may be increased alternately between two distractor units, i.e., distractor units on opposing sides of a vertebrae (e.g., FIG. 4D). In some embodiments, pressure can be monitored via pressure gauges which may be supplied with one and/or the other distractor units.

Figure 5A:
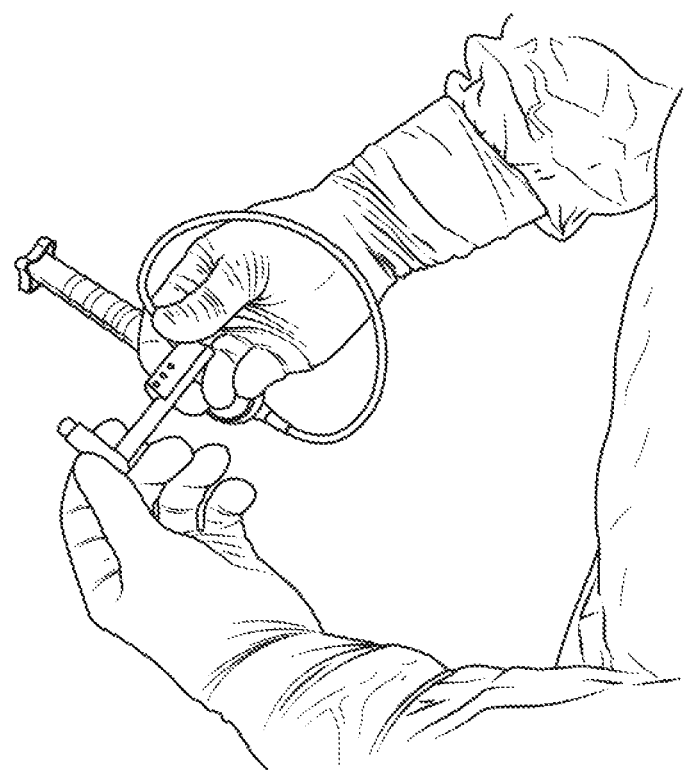
FIGS. 5A-D show example steps of the replacement of a distractor's piston with a longer piston for use in a corpectomy procedure, thereby facilitating the extension of the distractor to a suitable length for the procedure, according to some embodiments.
Figure 5B:
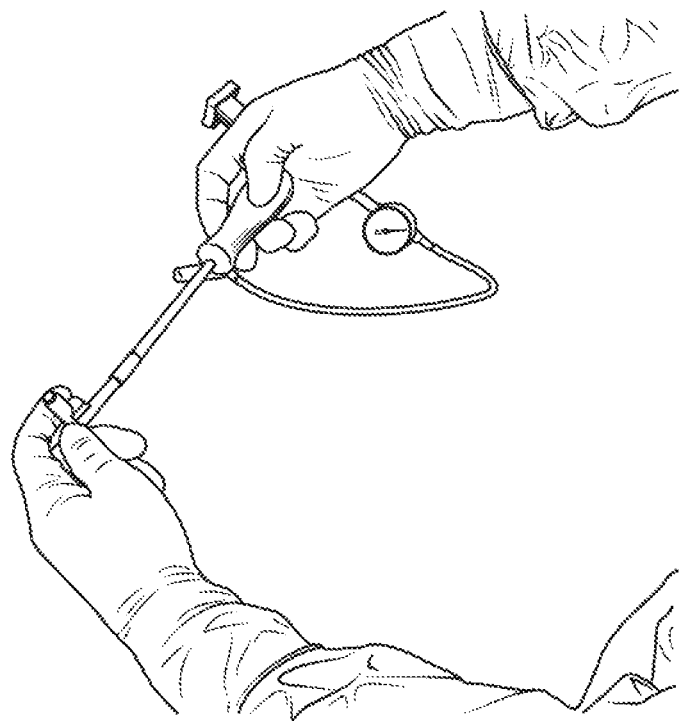
Figure 5C:
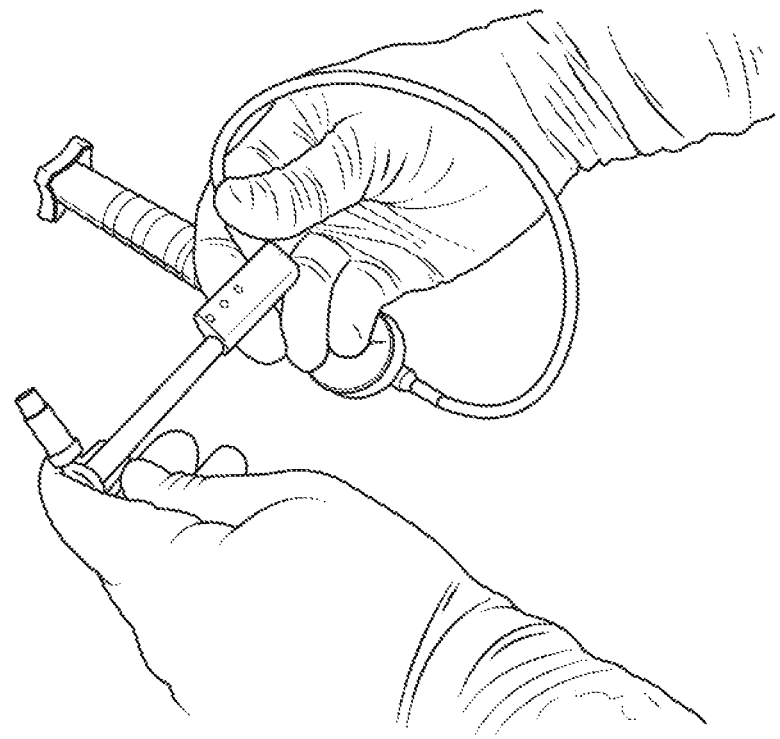
Figure 5D:
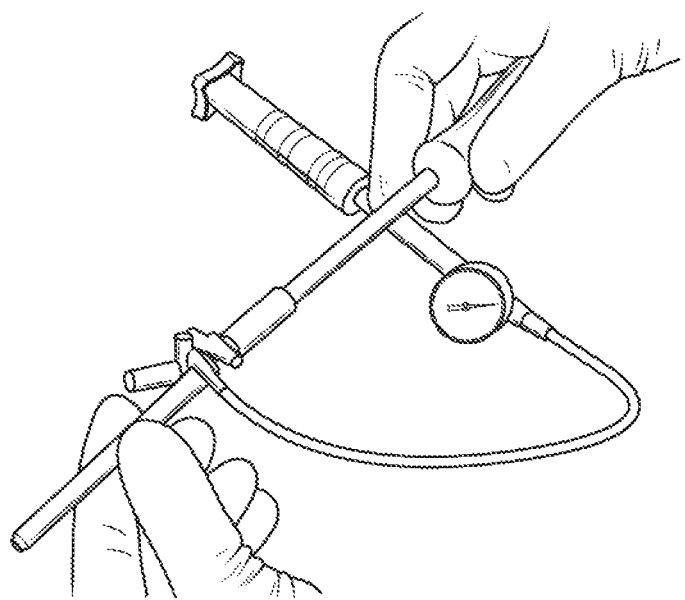

In some embodiments, a corpectomy may be performed using at least some of the steps discussed above with respect to a discectomy. In some embodiments, the same steps as in discectomy may be performed in the case of corpectomy, except for the use of longer distractor units to mount on vertebra that are farther apart from each other (compared to discectomy cases, for example). For example, longer distractor units may be used to remove some or all parts of a vertebral body. FIGS. 5A-D show example steps of the replacement of a distractor's piston with a longer piston for use in a corpectomy procedure, thereby facilitating the extension of the distractor to a suitable length for the procedure. The distractor units can be extended to a suitable length for the corpectomy procedure by replacing the hydraulic pistons associated therewith. In some embodiments, with reference to FIG. 5A, the piston assembly may be pulled out from its associated hydraulic cylinder barrel. Further, as shown in FIG. 5B, the piston may then be removed from the piston assembly, by using a designated screwdriver such as the one shown in FIG. 3J, for example. In some embodiments, a new longer piston may then be inserted into the piston assembly, as shown in FIG. 5C, for example, and secured by the requisite fasteners using a designated screwdriver, as shown in FIG. 5D, for example, and the distractor unit reassembled. In particular, the piston may be inserted into the hydraulic cylinder barrel, while ascertaining an O-ring seal is correctly positioned and in good condition. As discussed above, in some embodiments, the pistons may have a length ranging from about 30 mm to about 120 mm, from about 40 mm to about 100 mm, from about 50 mm to about 90 mm, from about 60 mm to about 80 mm, about 37 mm, about 47 mm, about 57 mm, about 77 mm, about 87 mm, about 100 mm, including values and subranges therebetween.

Figure 6A:
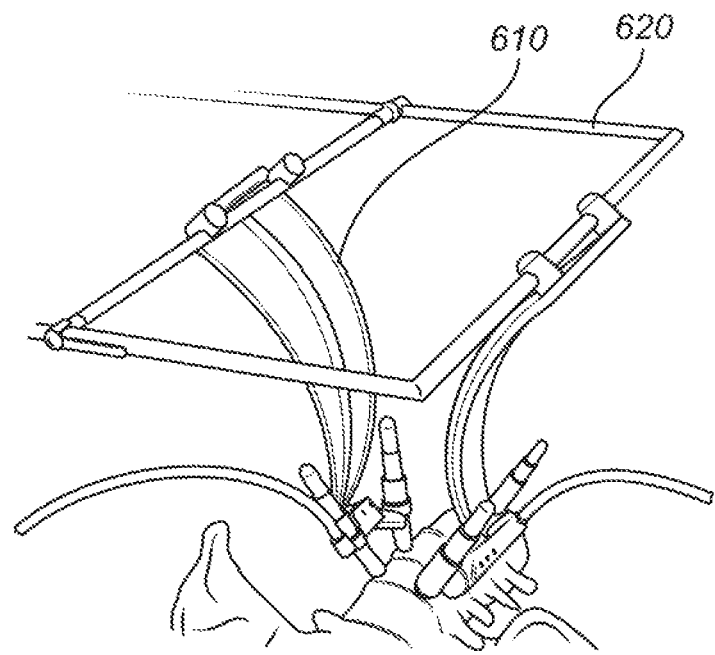
FIGS. 6A-F show the expansion of soft tissue retractors due to force exerted by a sliding frame to increase access to the spine during surgery, according to some embodiments.
Figure 6B:
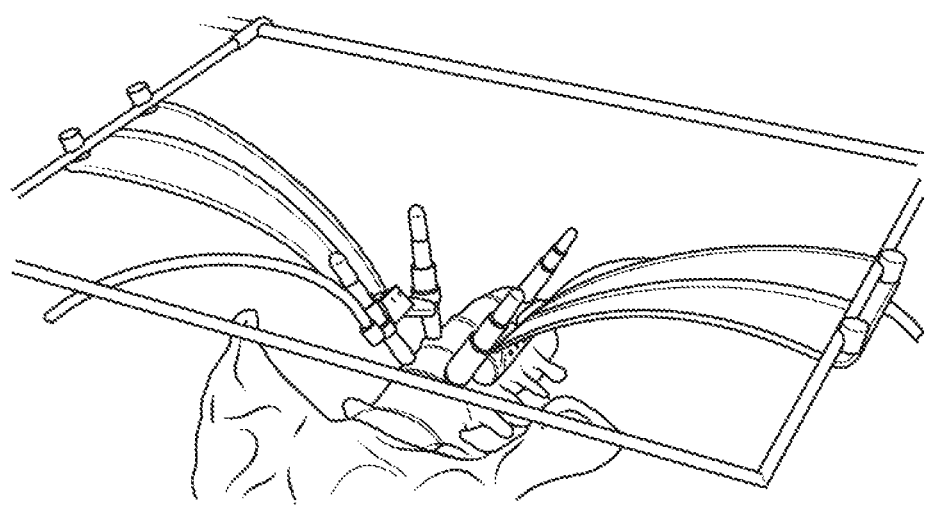

FIGS. 6A-D show the expansion of soft tissue retractors due to force exerted by a sliding frame to increase access to the spine during surgery, according to some embodiments. In some embodiments, access towards the region of interest (e.g., damaged disc) may be enhanced by using a tissue retractor that at least substantially isolates the vertebral body from the surrounding tissues. Such a retractor may also be beneficial in avoiding injuries to said surrounding tissues. For example, FIG. 6A shows a pair of retractors 610, one positioned on each side of the vertebrae of interest. In some embodiments, the retractor 610 may be configured to allow through x-ray, at least substantially, for example, when x-ray is being used to monitor the depth of bone screws. In some embodiments, hooks may be used to attach the retractors to the distractor to separate the soft tissues. In particular, hooks coupled to the retractors may be placed in designated openings/holes in each distractor unit, thereby positioning the retractors onto the distractor unit. A frame may then be positioned between the retractors to separate/expand the retractors and provide/improve accessibility to the vertebral body (i.e., spine).

Figure 6C:
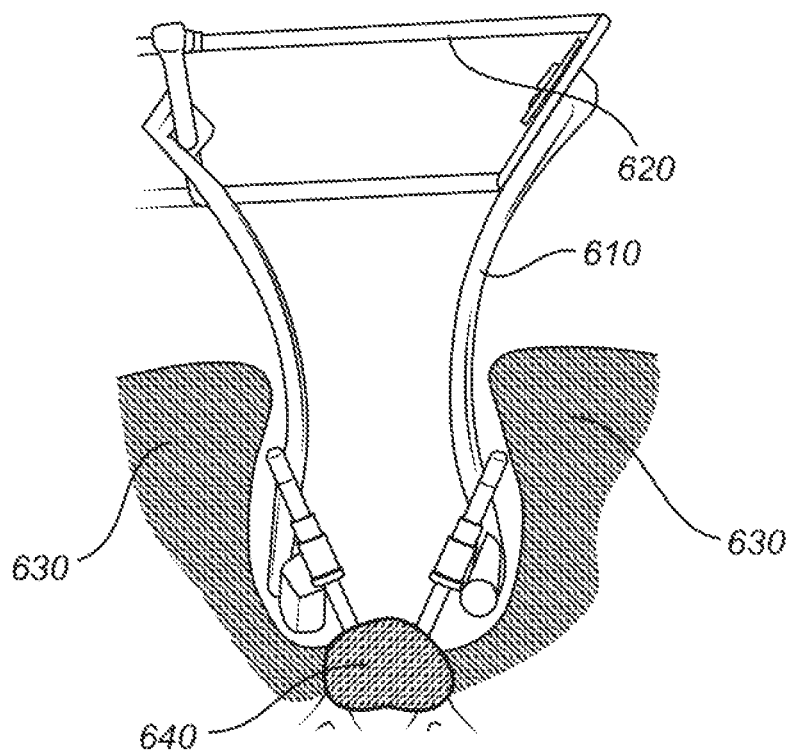
Figure 6D:
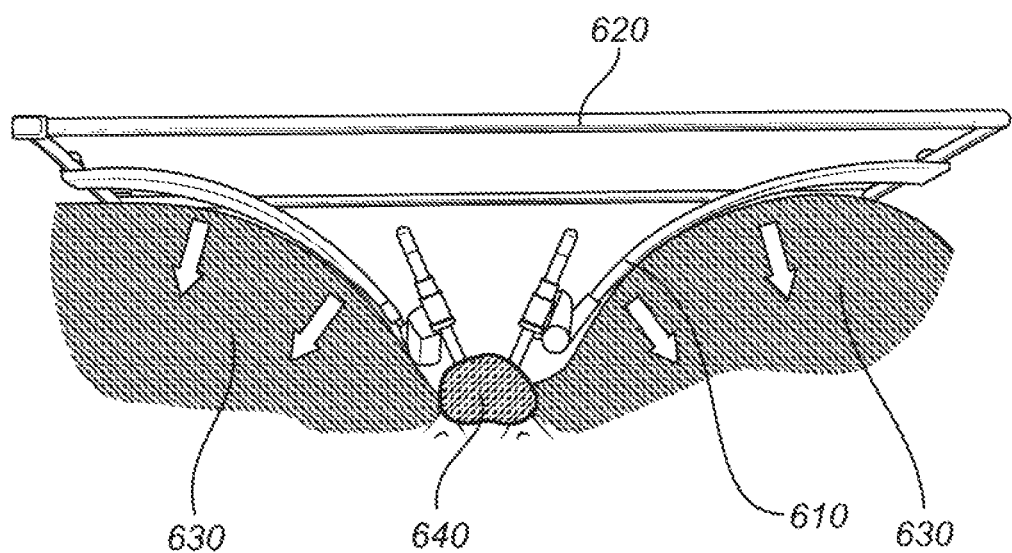
Figure 6E:
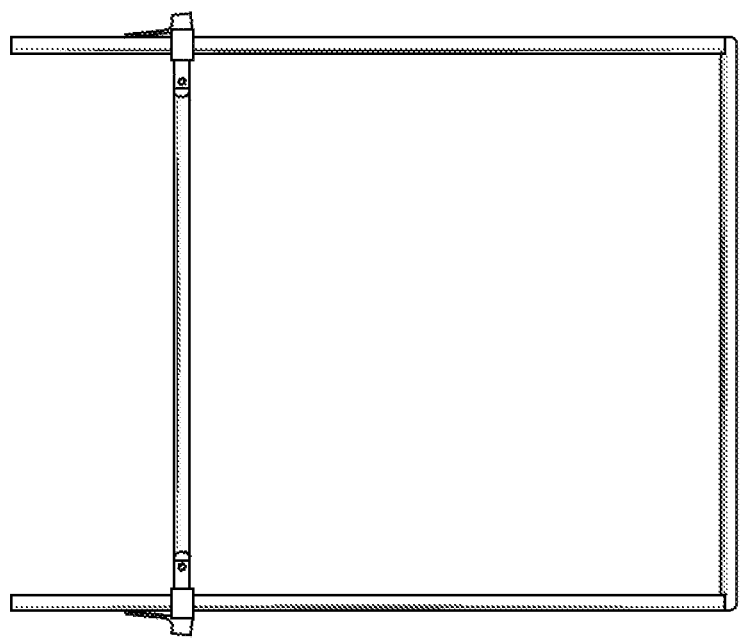
Figure 6F:
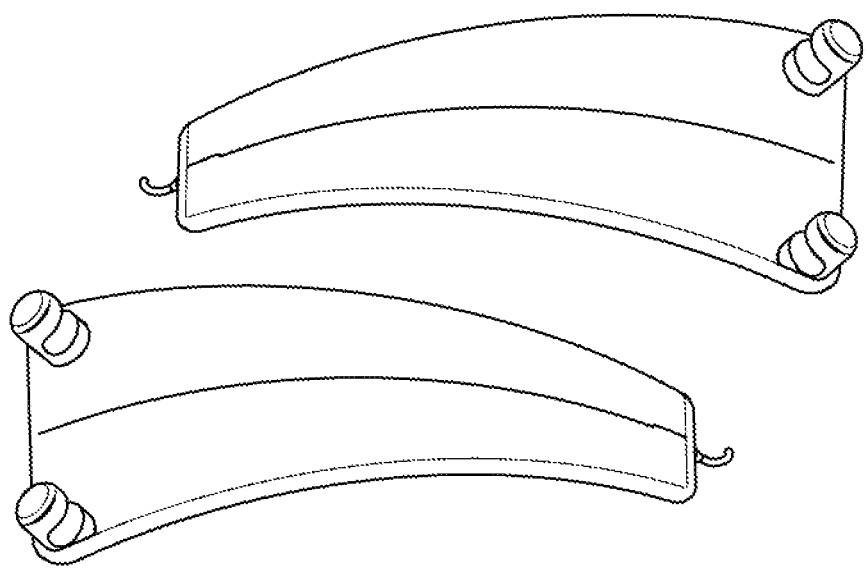

In some embodiments, the expansion of the retractors 610 is facilitated by a sliding frame 620 that is coupled to the pair of retractors and pushes the retractors 610 away from each other as the frame slides. For example, the sliding frame 620 may be a rectangular frame where one of the opposite side pair is configured to slide along the other side pair when expanding the retractors 610 away from each other, e.g., FIG. 6B. In general, the sliding frame is any structure that is configured to expand the pair of retractors 610 (facing each other) away from each other so that surrounding tissues are retracted away from the surgical region of interest (e.g., the region containing a damaged disc or vertebrae where the surgical procedure is focused at). Besides protecting the surrounding tissues, in some embodiments, the retractors 610 facilitate increased access to the surgical region of interest. For example, the retractors may decrease the depth of the spine or vertebra in the surgical region of interest. FIGS. 6C-D show example embodiment of the expansion of the retractors 610 under the force exerted by the sliding frame 620 as the sliding frame 620 slides. During the expansion, in some embodiments, the surrounding tissues 630 are retracted away from the vertebral body 640 of interest. FIGS. 6E-F show top views of example embodiments of a sliding frame and retractors disclosed herein, respectively.

Figure 7A:
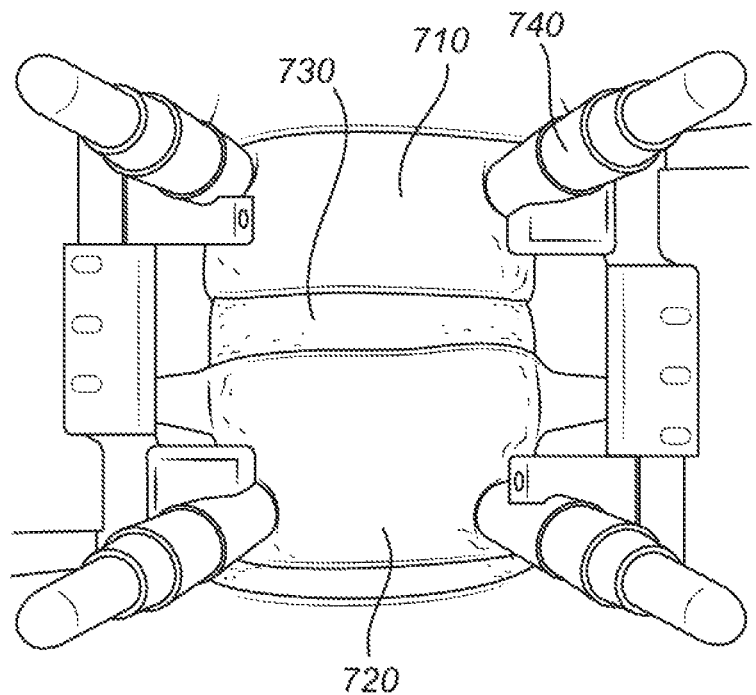
FIGS. 7A-B show the replacement of a defective or damaged disc with an implant using the hydraulic spinal distractor of FIGS. 1A-B during spine surgery, according to some embodiments.
Figure 7B:
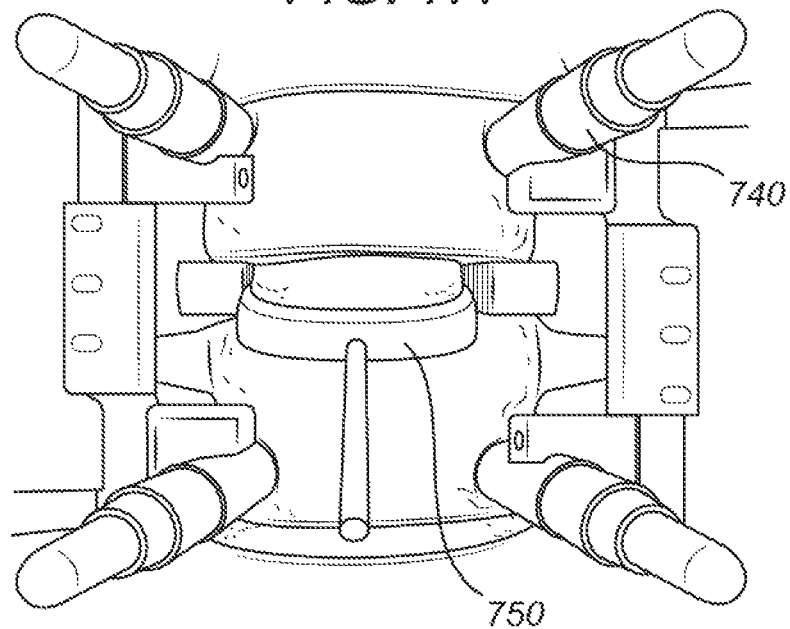

FIGS. 7A-B show the replacement of a defective or damaged disc with an implant using the hydraulic spinal distractor of FIGS. 1A-B during spine surgery, according to some embodiments. In some embodiments, the distance between neighboring vertebra 710 and 720 is controlled and varied by the distractor units 740. For example, the separation distance between the two vertebra 710 and 720 may be increased by using the distractor unit 740 to facilitate access to a damaged disc 730 and allow its replacement by an implant 750. The gap between the vertebra may be adjusted by turning one and/or both respective control handles of the distractor units 740. This allows for the hydraulic piston comprising the first arm 230 and the second arm 260 (FIG. 2A-F) to elongate as the first arm 230 retracts out of the hollow interior of the second arm 260. As the hydraulic piston elongates, in some embodiments, the separation between vertebra 710 and 720 increases, thereby increasing the width of their separation and providing enhanced access to the damaged disc 730. In some embodiments, the separation forces may be controlled manually. The distractor units may then be removed by reversing the above-noted steps.

In some embodiments, the vertebra 710 and 720 may not be neighboring vertebra, i.e., there may be a plurality of discs and one or more vertebra in between the vertebra 710 and 720. In such embodiments, the distractor units 740 control and manage the separation distance between the vertebra 710 and 720, providing access to the plurality of discs and the one or more vertebra. When replacing more than one disc, in some embodiments, the most inferior disc may be replaced first. In such embodiments, screws may be positioned in the superior vertebra to facilitate re-use of screw holes.

Figure 8A:
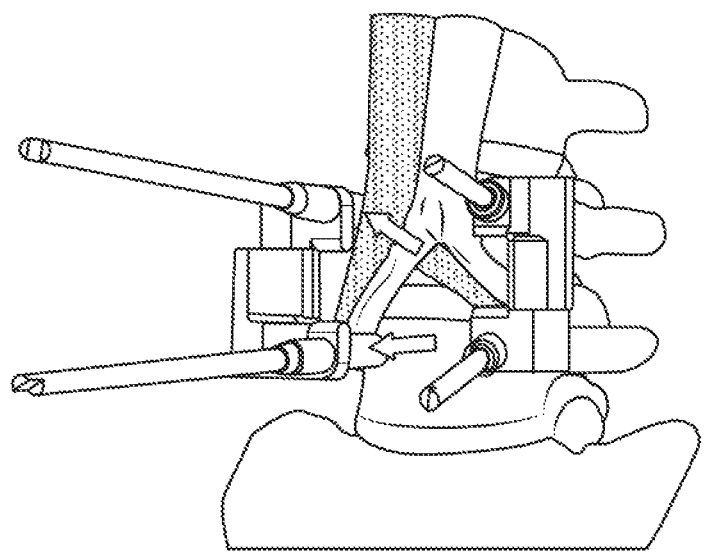
FIG. 8A-B show an example use of the hydraulic spinal distractor of FIGS. 1A-B to control the positioning of arteries and veins during surgery near aortic bifurcation, according to some embodiments.
Figure 8B:
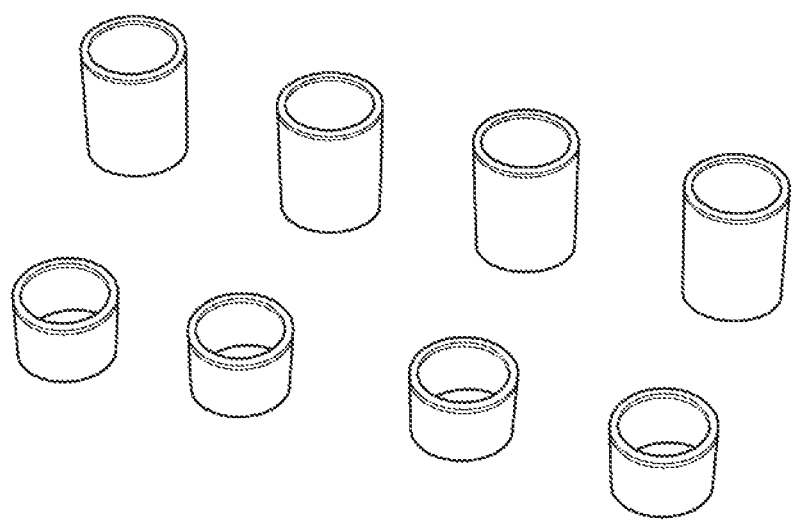

FIG. 8A-B show an example use of the hydraulic spinal distractor of FIGS. 1A-B to control the positioning of arteries and veins during surgery near aortic bifurcation, according to some embodiments. For example, screws, with spacer rings (an example embodiment of which are shown in FIG. 8B), can be used to control the position of the iliac arteries and veins during surgery in the region inferior to the aortic bifurcation. In some embodiments, the use of spacer rings of appropriate length allows for a sufficient gap(s) between the vertebrae and the distractor units so as to prevent compression of the vessels. In some embodiments, spacers may also protect the vessels from chafing on screw threads.

Example Application

As an example application, the hydraulic spinal distractor disclosed herein can be used in treatments that include with corpectomy, vertebral body replacement and fusion to treat spondylodiscitis of vertebra L1 and L2 discovered with the use of an MRI scan. The MRI can show progressive vertebral body destruction, indicated by a high MRI signal for fluid in disc space. Using an anterior approach, bone screws may be inserted or implanted to separate the vertebra surrounding the damaged body and stabilize during debridement and decompression/resection. Initially, the cortical structures of vertebra Th12 and L3 may be opened using an awl. Further, the bone screws may be inserted, for example, bi-cortically. Upon the insertion of the bone screws, the distractors may be mounted and an increase in hydraulic power distraction causes the vertebra to move away from each other, i.e., separate and hold apparat vertebral bodies. Once the vertebra are distanced from each other, debridement may occur to remove damaged tissues in the vicinity as well as corpectormy of vertebra L1 and L2. For example, a titanium mesh cage with lordotic end-plates may be assembled and filled up with bone graft and the mesh cage may be inserted and aligned with an x-ray. To allow compression on the cage, pressure in the hydraulic system may be decreased. Further, the distractor and the bone screws may be withdrawn and the insertion points of the screws may be sealed with bone wax. As a check, the length of the thoraco-lumbar plate Th12-L3 may be measured and fixed if desired. A later scan (e.g., CT scan about 6 months later) may be performed to determine if bone material has grown into the previously damaged region.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, components and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Still further, some embodiments disclosed herein are distinguishable over prior art references by specifically lacking one or more features disclosed in the prior art; that is, claims to such embodiments may include negative limitations so as to be distinguished from the prior art.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

[46] The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. A corpectomy method, comprising:
providing a distractor unit comprising at least a first hydraulic cylinder configured to removably receive a piston of a predetermined length during a surgical procedure;
providing the piston;
providing a plurality of bone screws;
affixing a first bone screw of the plurality of bone screws to a first vertebrae of a spine and a second bone screw of the plurality of bone screws to a second vertebrae of the spine;
mounting the distractor unit onto the first bone screw and the second bone screw; and
extending the hydraulic piston of the distractor unit to cause the first vertebrae and the second vertebrae to move away from each other.

2. The method of claim 1, further comprising providing a retractor, coupling the retractor to the distractor unit, and expanding the retractor to isolate the spine from at least some surrounding tissues.

3. The method of claim 2, wherein the retractor includes a frame configured to exert force on the retractor to cause its expansion.

4. The method of claim 2, wherein the retractor comprises a material that is at least translucent to X-rays.

5. The method of claim 1, wherein the distractor unit further comprises a spanner handle configured for controlling a pressure in the hydraulic cylinder.

6. The method of claim 5, wherein the distractor unit further comprises a pressure gauge configured for monitoring the pressure in the hydraulic cylinder.

7. The method of claim 1, wherein the first vertebrae of the spine and the second vertebrae of the spine are neighboring vertebra.

8. The method of claim 1, wherein at least one vertebrae exists between the first vertebrae of the spine and the second vertebrae of the spine.

9. The method of claim 1, wherein a length of the hydraulic piston ranges from 70 mm to 110 mm.

10. The method of claim 1, wherein the hydraulic piston is replaceable.

11. The method of claim 1, further comprising removing at least a part of a vertebral body located between the first vertebrae and the second vertebrae.

12. A vertebral separation method comprising:
  notching at least one pair of vertebrae to mark at least two pairs of positions for inserting bone screws at a lateral distance apart from a center of an anterior spinal column;
  inserting the bone screws into the at least one pair of vertebrae at the notched positions, the insertion configured at an angle relative to a longitudinal axis of the spinal column so as to avoid penetrating a spinal canal, and such that the bone screws enter, but not go through, opposite cortical bone tissue;
  mounting a suitably sized spacer ring to each of the bone screws;
  attaching a distractor unit to the bone screws in a substantially vertical position at a desired angle relative to an anterior side of the spinal column;
  locking each distractor unit at the desired angle against each pair of the bone screws; and
  separating the at least one pair of vertebrae by extending a hydraulic piston within the distractor unit such that the bone screws are moved away from each other.

13. The method of claim 12, wherein the distractor unit includes a handle configured to effect pressure control on the hydraulic piston and movement thereof.

14. The method of claim 12, wherein pressure is increased alternately between the distractor units located on opposite sides, and the lateral distance, apart from a center of the anterior spinal column.

15. The method of claim 12, wherein pressure is monitored via a pressure gauge included with one and/or another distractor unit.

16. The method of claim 12, further comprising positioning one or more retractors to tissue, wherein the retractors are configured to separate soft tissue.

17. The method of claim 16, wherein the retractors are placed in designated openings/holes in each distractor unit.

18. The method of claim 17, further comprising positioning a frame between the retractors, wherein the frame is configured to improve accessibility to the anterior spinal column.

19. The method of claim 12, further comprising performing a procedure selected from the group consisting of: corpectomy, insertion of disc prostheses, insertion of an anterior lumbar interbody fusion (ALIF) cage, and tumor removal.

20. The method of claim 12, further comprising adjusting a gap between the vertebrae by moving the hydraulic pistons.

* * * * *